US00PP35854P2

(12) United States Plant Patent
Li

(10) Patent No.: US PP35,854 P2
(45) Date of Patent: Jun. 4, 2024

(54) ***VERBENA* PLANT NAMED 'KLEVP22039'**

(50) Latin Name: ***Verbena* x *hybrida***
Varietal Denomination: KLEVP22039

(71) Applicant: KLEMM + SOHN GMBH & CO. KG, Stuttgart (DE)

(72) Inventor: Ruijun Li, North Parramatta (AU)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/326,213

(22) Filed: May 31, 2023

(51) Int. Cl.
*A01H 5/02* (2018.01)
*A01H 6/86* (2018.01)

(52) U.S. Cl.
USPC ..... Plt./308

(58) Field of Classification Search
USPC ..... Plt./308
CPC ..... A01H 5/02; A01H 5/00; A01H 6/86
See application file for complete search history.

(56) References Cited

PUBLICATIONS

Ball Seed Lascar Orange Lava *Verbena*, retrieved on Sep. 7, 2023 at https://www.ballseed.com/PlantInfo/?phid=063403829049707, one page. (Year: 2023).*
Manning 2022 Cast preview: Ball Horticultural Greenhous Management, retrieved on Sep. 7, 2023 at https://www.greenhousemag.com/news/cast-2022-preview-ball-horticultural/, 12 pp. (Year: 2022).*
Olvera A Return to Spring for Cast, retrieved on Sep. 7, 2023 at https://gpnmag.com/article/a-return-to-spring-for-cast/, 6 pp. (Year: 2022).*

* cited by examiner

*Primary Examiner* — June Hwu
(74) *Attorney, Agent, or Firm* — Weatherly IP Solutions, LLC; James M. Weatherly

(57) ABSTRACT

A new *Verbena* plant particularly distinguished by early, large, orange-red flowers with little white eyes and a semi-mounding to spreading plant habit, is disclosed.

1 Drawing Sheet

Genus and species: *Verbena* x *hybrida*.
Variety denomination: 'KLEVP22039'.

BACKGROUND OF THE NEW PLANT

The present invention comprises a new and distinct variety of *Verbena*, botanically known as *Verbena* x *hybrida*, and hereinafter referred to by the variety name 'KLEVP22039'. 'KLEVP22039' originated from a cross-pollination conducted in September 2015 in Cobbitty, New South Wales, Australia between the proprietary female *Verbena* variety '14.0109' (unpatented), and the proprietary male *Verbena* variety '14.00T2' (unpatented).

The seeds from the cross were sown and plants were grown for evaluation, where an individual plant designated 'KLEVP22039' was selected from the group of plants in Cobbitty, New South Wales, Australia in October 2016.

In October 2016, 'KLEVP22039' was first vegetatively propagated by vegetative cuttings in Cobbitty, New South Wales, Australia. 'KLEVP22039' was found to reproduce true to type in successive generations of asexual propagation via vegetative cuttings.

SUMMARY

The following are the most outstanding and distinguishing characteristics of this new variety when grown under normal horticultural practices in Latina, Italy.

1. Early, large, orange-red flowers with little white eyes; and
2. A semi-mounding to spreading plant habit.

DESCRIPTION OF THE PHOTOGRAPH

This new *Verbena* plant is illustrated by the accompanying photograph which shows the plant's overall plant habit including form, buds, foliage, and flowers. The photograph is of a plant approximately 12-weeks-old grown indoors in Stuttgart, Germany in May 2021. The colors shown are as true as can be reasonably obtained by conventional photographic procedures.

DESCRIPTION OF THE NEW VARIETY

The following detailed descriptions set forth the distinctive characteristics of 'KLEVP22039'. The data which define these characteristics were collected from asexual reproductions carried out in Latina, Italy. Data was collected on three-month-old plants grown in 2019. Color references are to The R.H.S. Colour Chart of The Royal Horticultural Society of London (R.H.S.), 5$^{th}$ edition (2007).

Classification:
- *Family*.—Verbenaceae.
- *Botanical*.—*Verbena* x *hybrida*.
- *Common*.—*Verbena*.
- *Designation*.—'KLEVP22039'.

Parentage:
- *Female parent*.—'14.0109' (unpatented).
- *Male parent*.—'14.00T2' (unpatented).

Plant:
- *Growth and branching habit*.—Semi-mounding to spreading.
- *Height* (*from top of soil*).—20.0 cm.
- *Width* (*horizontal plant diameter*).—38.0 cm.
- *Time to produce a finished flowering plant*.—8 weeks.
- *Time to initiate and develop roots*.—2 weeks.

*Root description*.—RHS 155B (White), fine fibrous roots.

Stems:

*Number of branches per plant*.—More than 15.
*Growth habit*.—Semi-mounding to spreading.
*Length*.—24.0 cm.
*Diameter*.—0.21 cm.
*Internode length*.—2.1 cm.
*Color*.—RHS 139D (Green).
*Anthocyanin*.—Absent.
*Texture*.—Pubescent.
*Appearance in cross-section*.—Round.

Leaves:

*Arrangement*.—Opposite.
*Immature and mature leaf color*.—Upper surface: RHS 141A (Green). Lower surface: RHS 141C (Green).
*Length*.—4.6 cm.
*Width*.—2.3 cm.
*Shape*.—Lanceolate.
*Apex*.—Acute.
*Base*.—Obtuse.
*Margin*.—Crenate.
*Texture* (*both upper and lower surfaces*).—Pubescent.
*Venation type*.—Pinnate.
*Venation color* (*both upper and lower surfaces*).—RHS 141D (Green).
*Anthocyanin*.—Absent.
*Petioles*.—Length: 0.1 cm. Diameter: 0.1 cm. Color: RHS 141D (Green). Texture: Leathery.

Flower buds:

*Shape*.—Tall, cylindrical.
*Length*.—1.4 cm.
*Diameter*.—0.3 cm.
*Color* (*at tight bud*).—RHS 39B.

Inflorescence:

*Shape*.—Broad ovate.
*Blooming habit* (*flowering season*).—Continuously.
*Lastingness of individual blooms on the plant*.—About 1 week.
*Fragrance*.—Absent.
*Inflorescence type*.—Umbel.
*Length of inflorescence*.—3.5 cm.
*Diameter of inflorescence*.—5.2 cm.
*Number of florets per inflorescence*.—22.
*Peduncle*.—Color: RHS 141A (Green). Length: 2.2 cm. Diameter: 0.15 cm. Texture: Pubescent.

Florets:

*Length*.—2.4 cm.
*Diameter*.—2.1 cm.
*Color*.—Immature: Upper surface: Orange red RHS N30A with little white eyes (RHS 155A) at center of floret. Lower surface: RHS 41A. Mature: Upper surface: Orange red RHS N30B with little white eyes (RHS 155A) at center of floret. Lower surface: RHS 41B.
*Texture*.—Soft.
*Form*.—Single.
*Corolla tube length*.—1.7 cm.
*Corolla tube color*.—RHS 157B (Green-White).
*Petals*.—Length of lobe: 1.3 cm. Diameter of lobe: 0.8 cm. Lobe shape: Obtuse. Arrangement of the corolla lobes: Free. Corolla lobes curvature of longitudinal axis: Straight. Apex: Emarginate. Base: Fused to from tube. Margin: Entire. Texture (both upper and lower surfaces): Glossy, satiny.
*Pedicels*.—Not visible.

Sepals:

*Shape*.—Lanceolate.
*Apex*.—Acute.
*Base*.—Obtuse.
*Margin*.—Entire.
*Length*.—1.2 cm.
*Diameter*.—0.2 cm.
*Color*.—RHS 142C (Green).
*Texture* (*both upper and lower surfaces*).—Hairy, dull.

Reproductive organs:

*Stamens*.—Present. Quantity: 4. Color: RHS 139D (Green). Filament length: 0.2 cm. Filament diameter: 0.1 cm. Anther: Shape: Elliptic. Color: RHS 141D (Green). Length: 0.15 cm. Diameter: 0.1 cm. Pollen amount: Sparse.
*Pistils*.—Quantity: 1. Length: 1.8 cm. Diameter: 0.1 cm. Stigma: Color: RHS 141D (Green). Appearance: Ovate. Length: 0.1 cm. Diameter: 0.1 cm. Style: Color: RHS 141D (Green). Length: 1.7 cm. Diameter: 0.1 cm.

Fruit and seed set: None observed to date.

Disease and pest/insect resistance: Good tolerance to powdery mildew (*Podosphaera xanthii*).

COMPARISON WITH PARENTAL LINES AND KNOWN VARIETY

'KLEVP22039' is distinguished from its parents as described in Table 1.

TABLE 1

Comparison with Parental Lines

| Characteristic | 'KLEVP22039' | Female parent '14.0109' | Male parent '14.00T2' |
|---|---|---|---|
| Flower color | Orange red with little eyes | Pink | Orange red |
| Flower size | Smaller than '14.0109' | Bigger than 'KLEVP22039' | Smaller than 'KLEVP22039' |

'KLEVP22039' is most similar to the commercial *Verbena* variety 'KLEVP15474' (U.S. Plant Pat. No. 28,454). Differences between the varieties are described in Table 2.

TABLE 2

Comparison with Similar Variety

| Characteristic | 'KLEVP22039' | 'KLEVP15474' |
|---|---|---|
| Flower color | Orange red (RHS N30B) with little white eyes (RHS 155A) | Red (RHS 38B) with red eyes (RHS 52A) |
| Earliness | Earlier than 'KLEVP15474' | Later than 'KLEVP22039' |

I claim:

1. A new and distinct cultivar of *Verbena* Plant Named 'KLEVP22039' as described and illustrated herein.

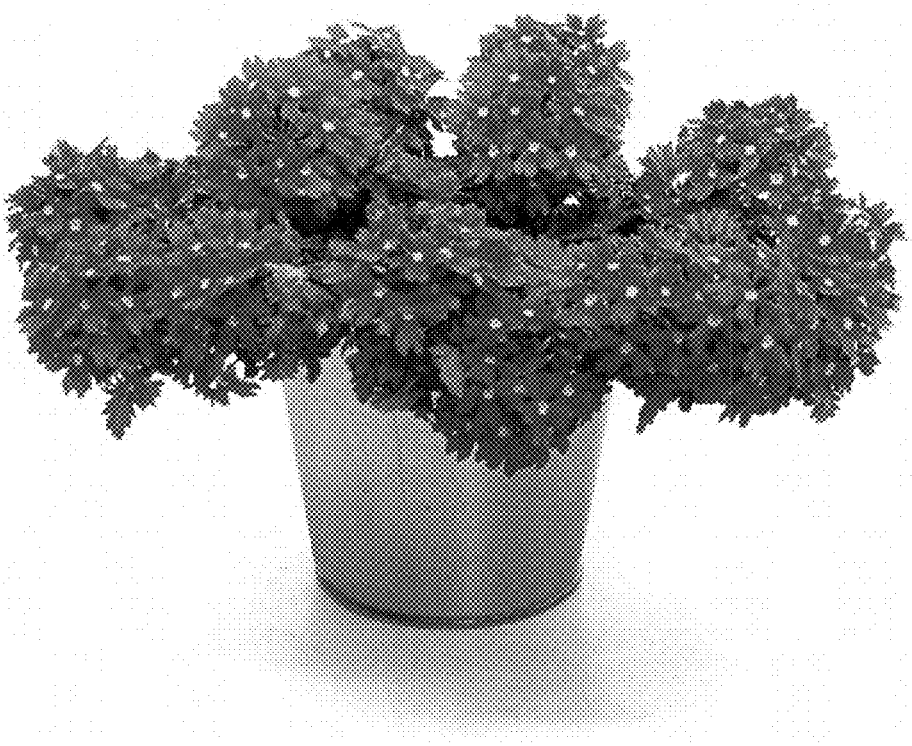

* * * * *